US011326142B2

(12) United States Patent
Patil et al.

(10) Patent No.: US 11,326,142 B2
(45) Date of Patent: May 10, 2022

(54) BIOMANUFACTURING APPARATUS

(71) Applicant: Global Life Sciences Solutions USA LLC, Marlborough, MA (US)

(72) Inventors: Haresh Digambar Patil, Bangalore (IN); Anoop Bhargav, Bangalore (IN); Praveen Paul, Bangalore (IN); Sebastian John, Bangalore (IN)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 525 days.

(21) Appl. No.: 15/755,086

(22) PCT Filed: Aug. 25, 2016

(86) PCT No.: PCT/EP2016/070076
§ 371 (c)(1),
(2) Date: Feb. 25, 2018

(87) PCT Pub. No.: WO2017/032830
PCT Pub. Date: Mar. 2, 2017

(65) Prior Publication Data
US 2018/0251722 A1 Sep. 6, 2018

(30) Foreign Application Priority Data

Aug. 25, 2015 (IN) ........................... 2632/DEL/2015
Oct. 19, 2015 (GB) ..................................... 1518426
Apr. 29, 2016 (IN) ............................. 201611015089

(51) Int. Cl.
*C12M 1/00* (2006.01)
*C12M 1/36* (2006.01)
*C12M 3/06* (2006.01)

(52) U.S. Cl.
CPC ............ *C12M 41/48* (2013.01); *C12M 23/02* (2013.01); *C12M 27/16* (2013.01); *C12M 41/14* (2013.01)

(58) Field of Classification Search
CPC ...................................................... C12M 41/14
See application file for complete search history.

(56) References Cited

U.S. PATENT DOCUMENTS 4,336,329 A * 6/1982 Hesse .................... C12M 41/14
422/298
8,383,395 B2 2/2013 Hata et al.
(Continued)

FOREIGN PATENT DOCUMENTS

CN 101603006 A 12/2009
CN 102556466 A 7/2012
(Continued)

OTHER PUBLICATIONS

International Search Report and the Written Opinion of the International Searching Authority, or the Declaration from International Appl. No. PCT/EP2016/070076, dated Nov. 4, 2016.
(Continued)

*Primary Examiner* — Jonathan M Hurst
(74) *Attorney, Agent, or Firm* — Eversheds Sutherland (US) LLP

(57) ABSTRACT

Disclosed is a biomanufacturing apparatus (1) comprising a housing (20) including top (22) and bottom (24) faces which allow stacking of plural housings, an access door (25) at a front side of the housing, a substantially enclosed bioreactor chamber (30) inside the housing accessible via the door, and a further substantially enclosed region (36) inside the housing containing electrical parts and/or electronic control components, the chamber (30) including: a tray (40/240) for supporting a bioreactor, a tray support (45/245) including a mechanism (44,47/244,247) for rocking the tray in use; the
(Continued)

tray having complementary formations allowing movement of tray relative to the tray support toward the front side to allow more convenient access to the bioreactor.

15 Claims, 13 Drawing Sheets

(56) References Cited

U.S. PATENT DOCUMENTS

| | | | |
|---|---|---|---|
| 10,676,705 B2 | 6/2020 | Henon et al. | |
| 2006/0128005 A1 | 6/2006 | Hasegawa et al. | |
| 2006/0191893 A1* | 8/2006 | Weinfield | B01D 61/18 219/428 |
| 2009/0037031 A1 | 2/2009 | George et al. | |
| 2011/0014689 A1* | 1/2011 | Gandlur | B01F 11/0028 435/289.1 |
| 2011/0207209 A1 | 8/2011 | Hammons et al. | |
| 2012/0258441 A1* | 10/2012 | Gebauer | C12M 23/14 435/3 |
| 2013/0157355 A1* | 6/2013 | Barrett | C12M 27/16 435/325 |
| 2013/0251483 A1 | 9/2013 | Kobayashi et al. | |
| 2013/0316446 A1* | 11/2013 | Andersson | B01F 11/0017 435/305.1 |
| 2018/0002650 A1* | 1/2018 | Han | C12M 41/48 |
| 2018/0250666 A1 | 9/2018 | Paul et al. | |

FOREIGN PATENT DOCUMENTS

| | | |
|---|---|---|
| CN | 103361271 A | 10/2013 |
| EP | 2607474 A1 | 6/2013 |
| JP | H037575 A | 1/1991 |
| WO | 2013135817 A1 | 9/2013 |
| WO | 2015048712 A2 | 4/2015 |
| WO | 2017032830 A1 | 3/2017 |

OTHER PUBLICATIONS

Great Britain Search Report from GB Appl. No. GB1518426.0, dated Jul. 26, 2016.

Celltainer Biotech, "Cell-tainer single-use bioreactor for cell cultures—CM2SCEU/CM2SCUS", celltainer.com, [online], Available from: http://celltainer.com/wp-content/uploads/2015/01/cell-culture.pdf [Accessed Jul. 22, 2016] See particularly System Specifications.

Japanese Office Action for JP Application No. 2018-510088 dated Jun. 15, 2020 (10 pages with English translation).

GE Healthcare Life Sciences, "WAVE Bioreactor 2/10 and 20/50 systems," 2011, Data file 28-9520-58 AB, pp. 1-6.

Chinese Office Action for CN Application No. 201680062250.5 dated Feb. 5, 2021 (17 page, with English translation).

Japanese Office Action for JP Application No. 2018-510088 dated Apr. 12, 2021 (11 pages, with English translation).

* cited by examiner

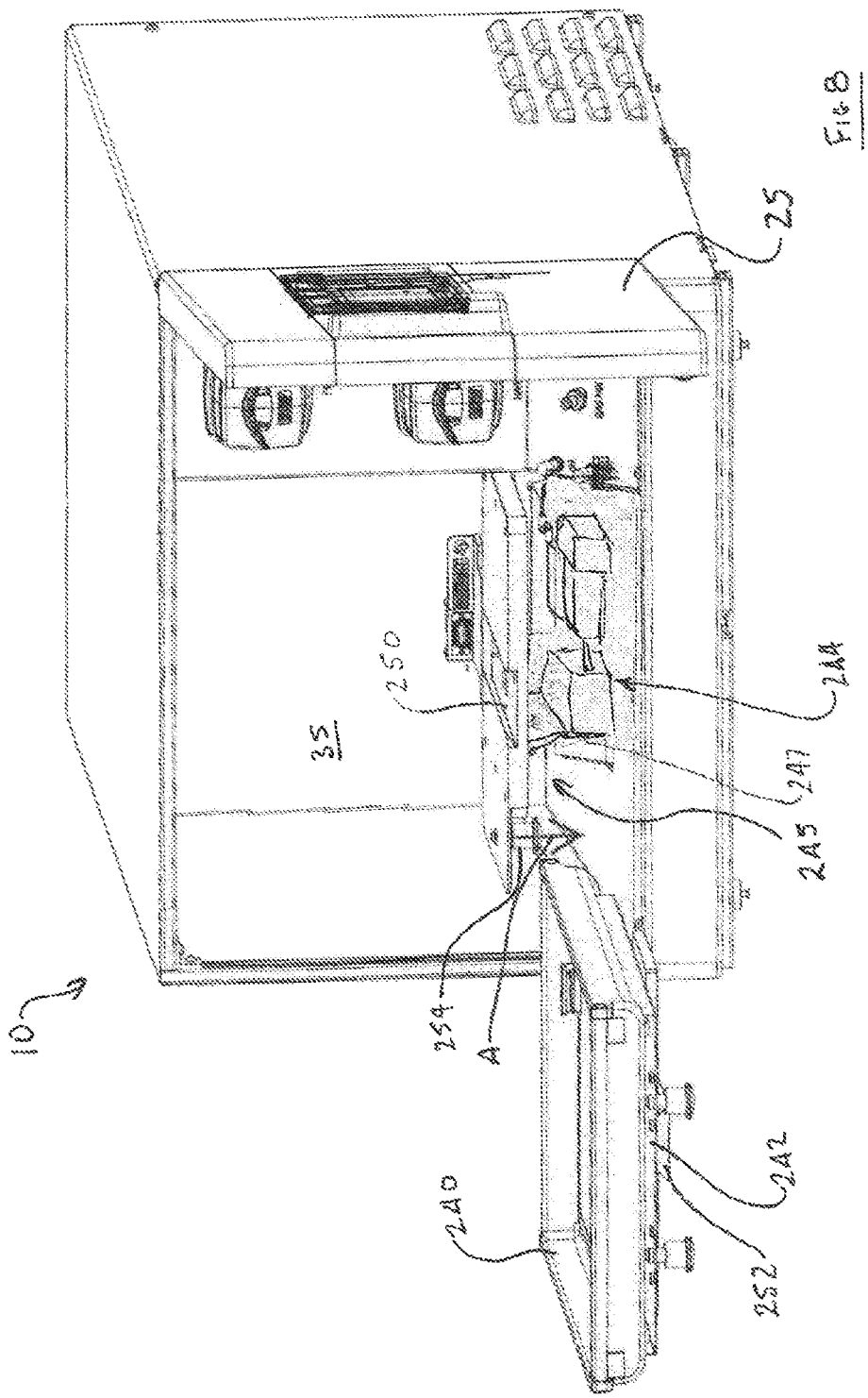

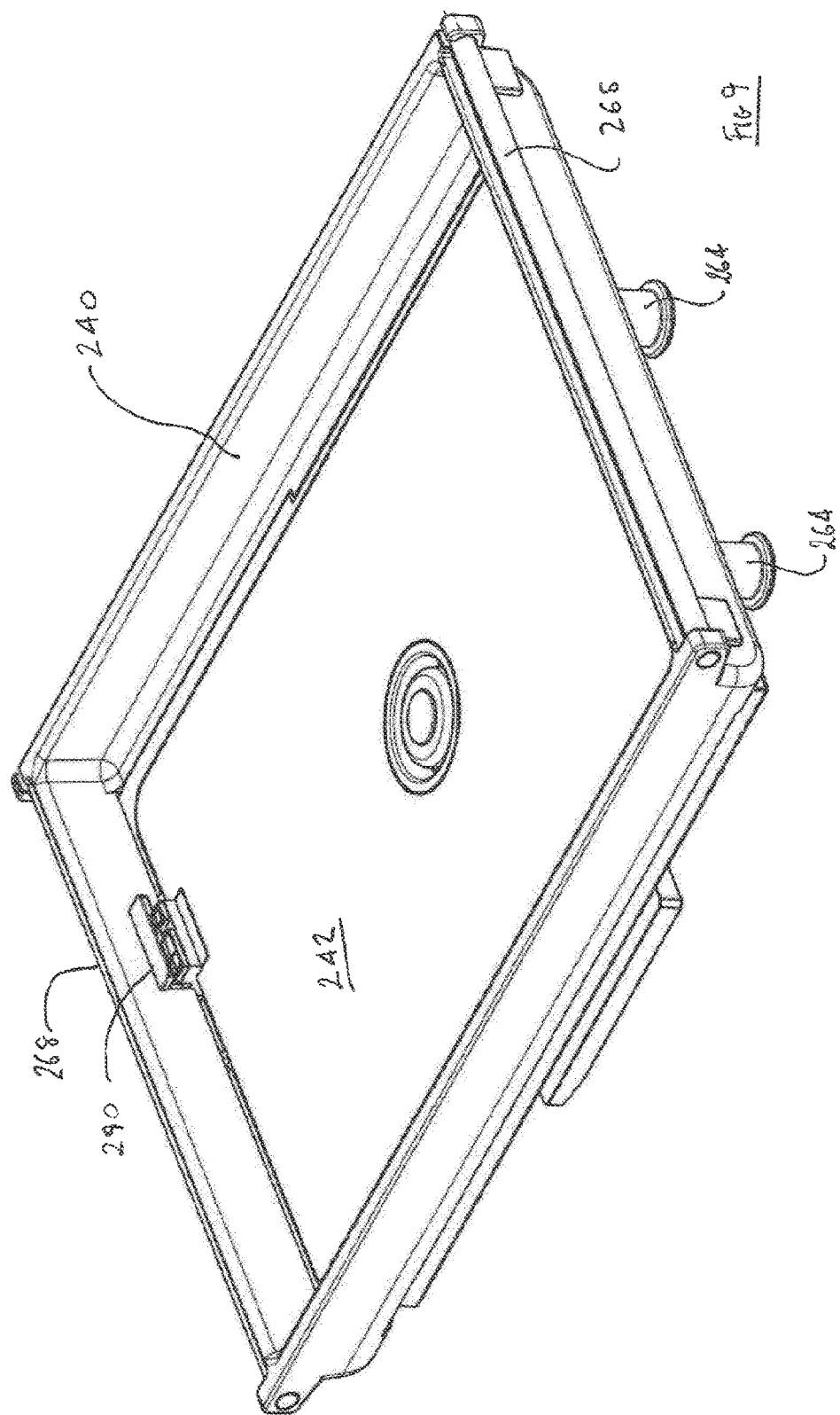

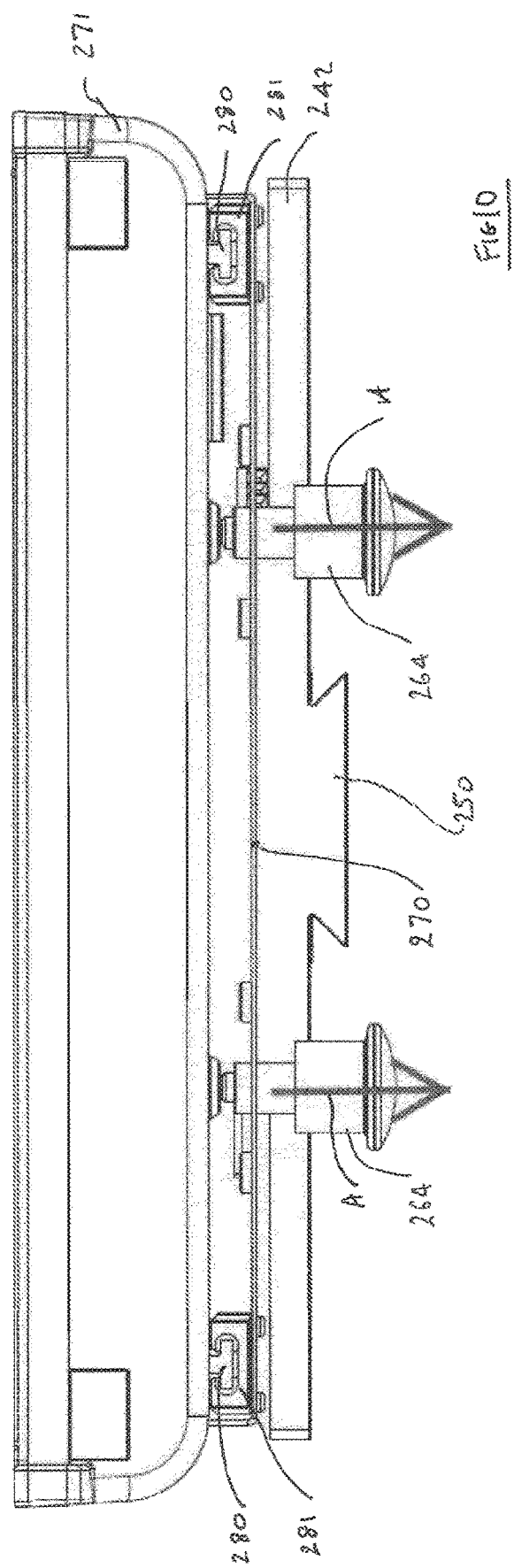

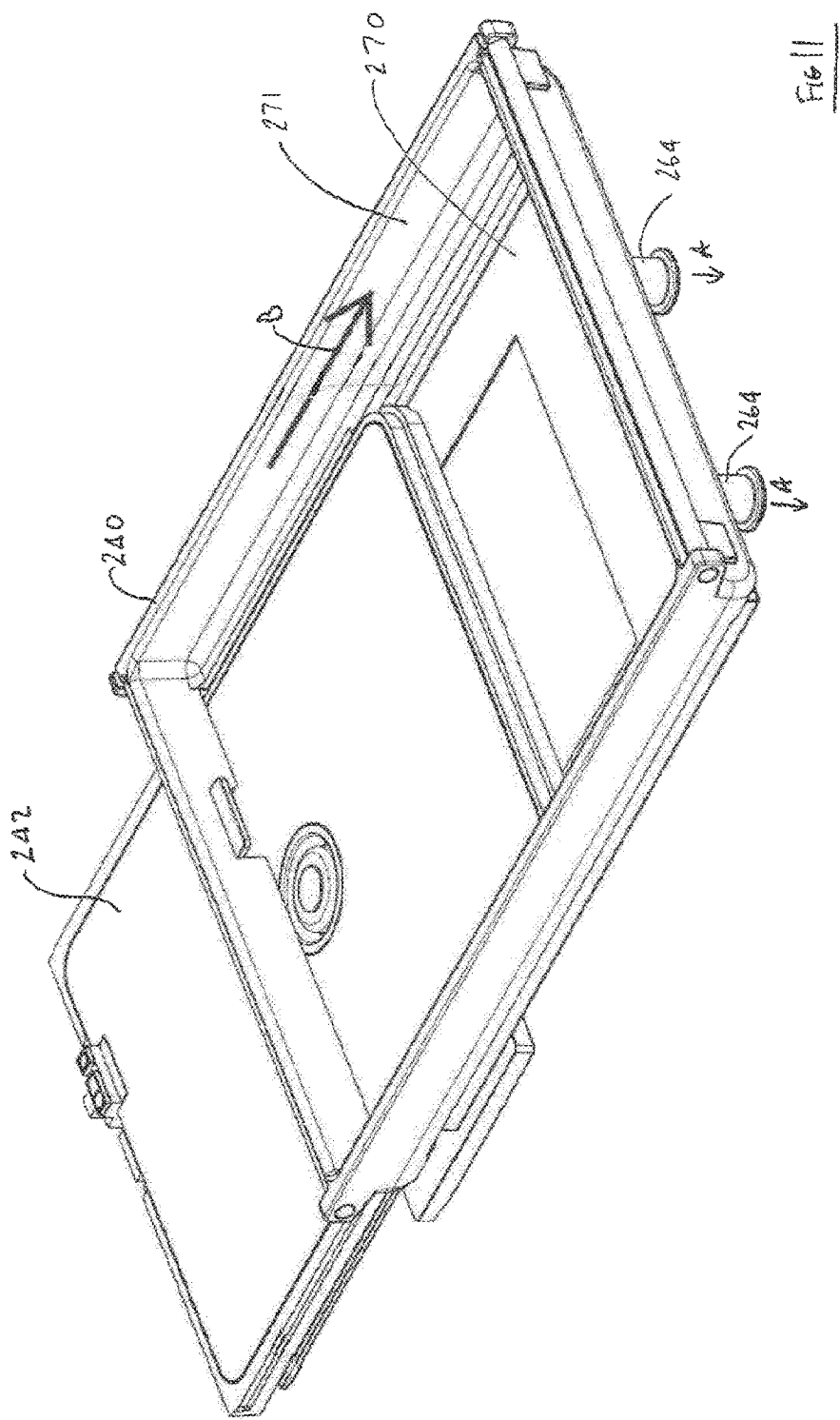

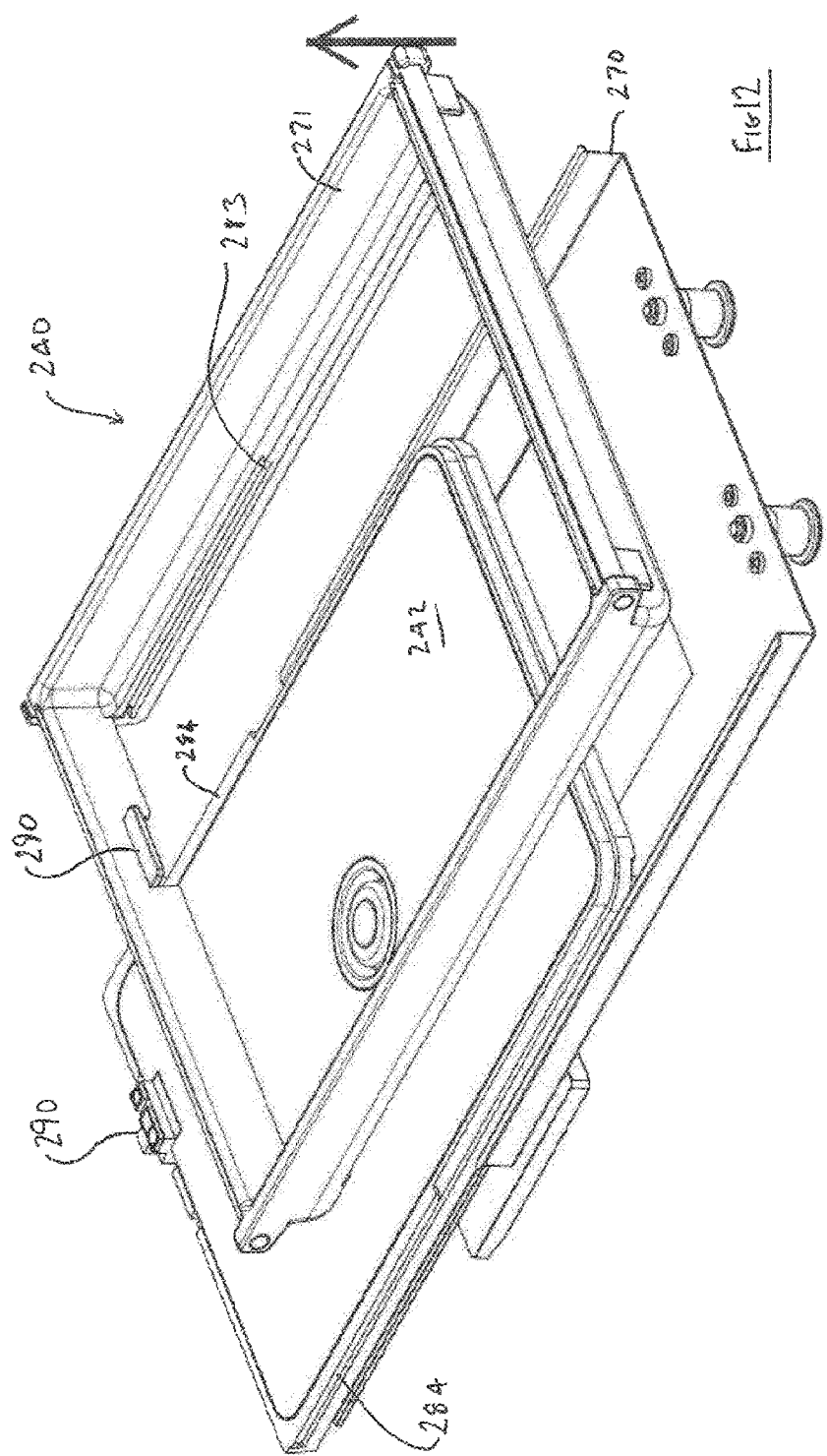

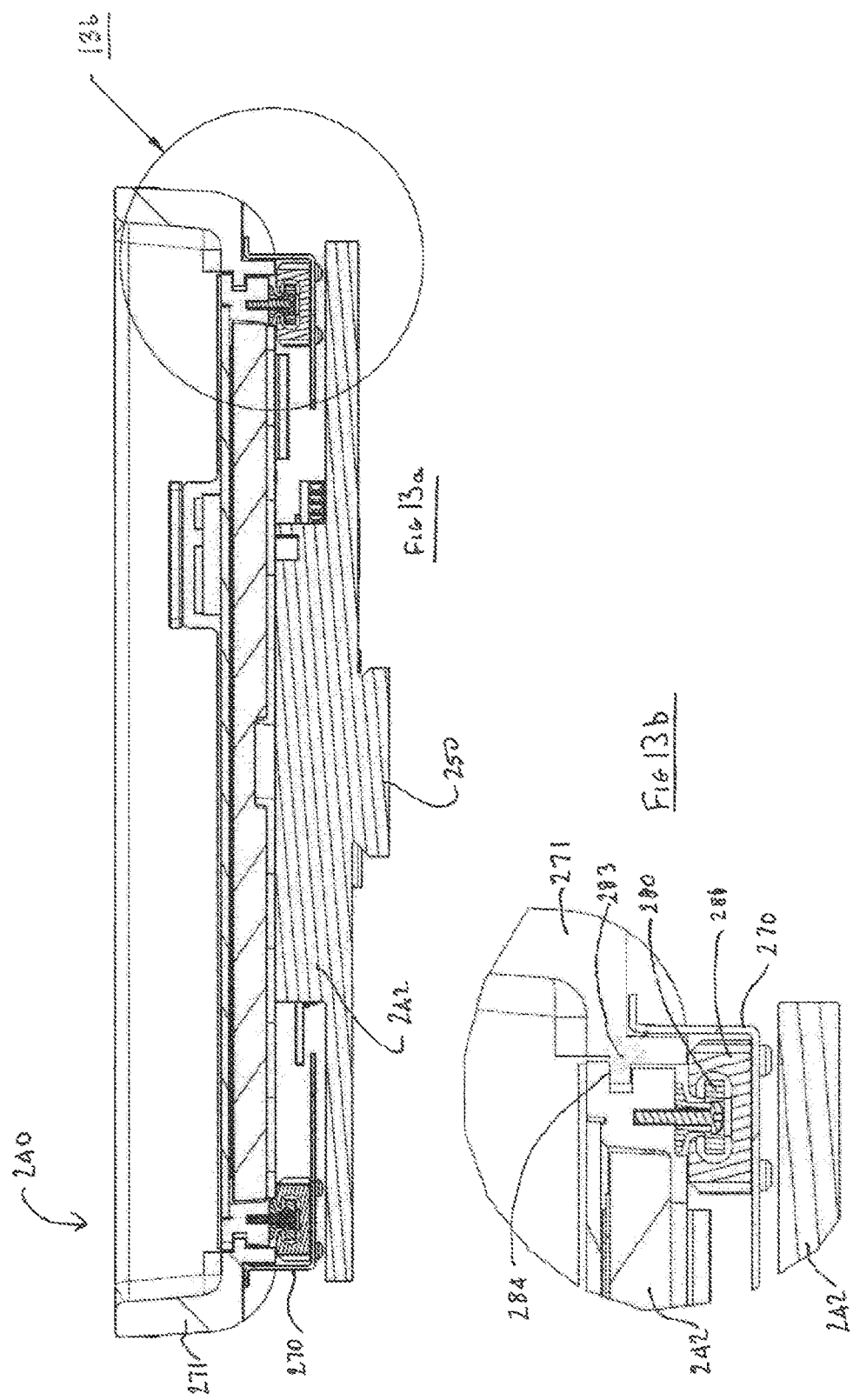

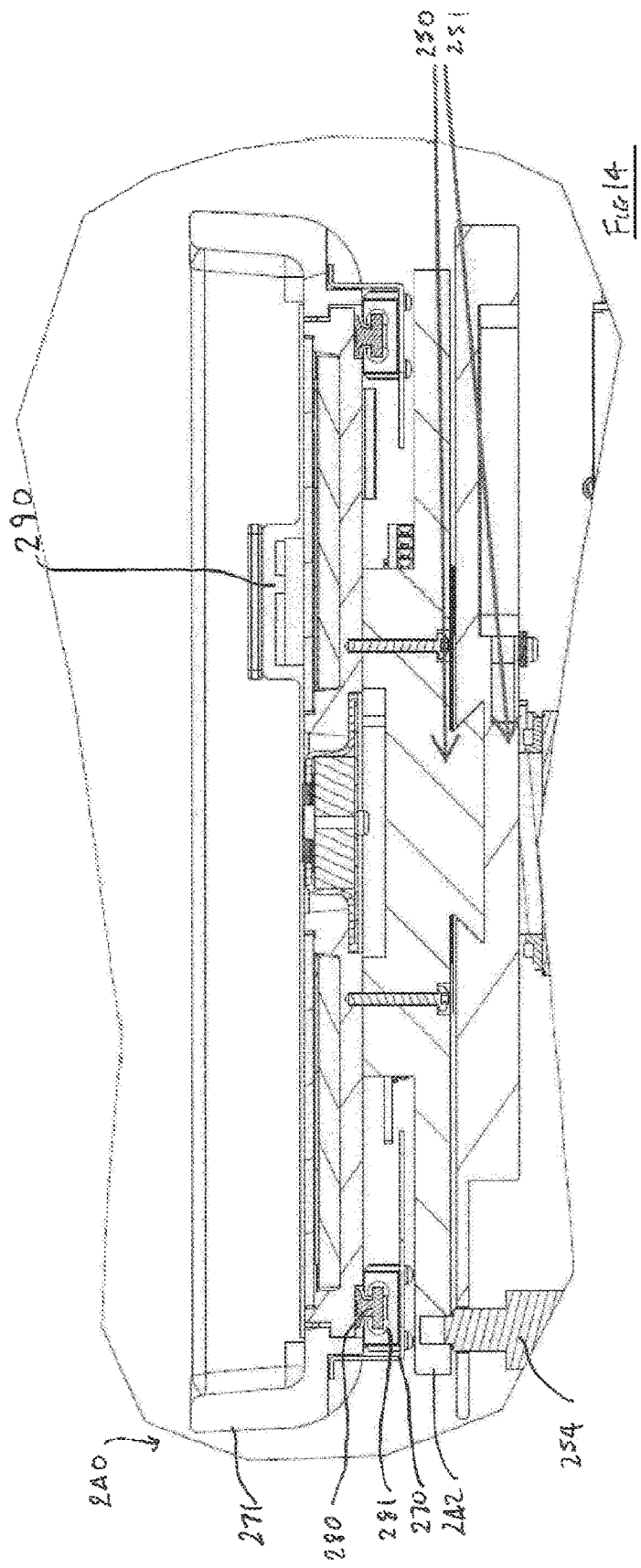

BIOMANUFACTURING APPARATUS

FIELD OF THE INVENTION

The present invention relates to biomanufacturing apparatus, for example for cell culturing. In particular, the invention relates to bioreactor apparatus in the form of single instruments, and plural instruments arranged into a biomanufacturing system for optimising the usage of laboratory and cell culturing space for biomanufacturing.

BACKGROUND OF THE INVENTION

Cell culture, for example the culture of mammalian, bacterial or fungal cells, may be carried out to harvest the living cells for therapeutic purposes and/or to harvest biomolecules, such as proteins or chemicals (e.g. pharmaceuticals) produced by the cells. As used herein, the term "biomolecule" can mean any molecule, such as a protein, peptide, nucleic acid, metabolite, antigen, chemical or biopharmaceutical that is produced by a cell or a virus. Herein, the term biomanufacturing is intended to encompass the culturing or multiplication of cells, and the production of biomolecules. The term bioreactor is intended to encompass a generally enclosed volume capable of being used for biomanufacturing.

The cells are generally grown in large scale (10,000 to 25,000 litre capacity) bioreactors which are sterilisable vessels designed to provide the necessary nutrients and environmental conditions required for cell growth and expansion. Conventional bioreactors have glass or metal growth chambers which can be sterilized and then inoculated with selected cells for subsequent culture and expansion. Media within the growth chambers are often agitated or stirred by the use of mechanical or magnetic impellers to improve aeration, nutrient dispersal and waste removal.

In recent years, there has been a move towards 'single use' bioreactors which offer smaller batch sizes, greater production flexibility, ease of use, reduced capital cost investment and reduced risk of cross-contamination. These systems can also improve the efficiency of aeration, feeding and waste removal to increase cell densities and product yields. Examples include WAVE™ bags (GE Healthcare) mounted on rocking platforms for mixing, or stirred-tank single-use vessels such as those available from Xcellerex Inc (GE Healthcare). With the advent of 'personalised medicine', autologous cell therapies requiring many small batches of cells to treat patients with unique cell therapies has become important.

Manufacturing facilities, such as tissue culture laboratories, for the production of cells and biomolecules, have traditionally been custom designed and carried out in clean environments to reduce the risk of contamination. Such facilities are costly to run and maintain and also to modify if priorities or work demands change. Work stations for maintaining or harvesting the cells within the bioreactors require a specific 'footprint' which occupies a significant floor space in the culture laboratory. As the workstations spend much of their time unattended, while the cells are growing in the bioreactors, the laboratory space is not efficiently or effectively used.

An improvement is proposed in WO 2014122307, wherein the laboratory space required for cell culture is reduced by the provision of customised workstations and storage bays for bioreactors, on which, conventional WAVE type bioreactors and ancillary equipment can be supported. Large supporting frameworks are required for that equipment.

U.S. Pat. No. 6,475,776 is an example of an incubator for cell culture dishes, which has a single incubator housing and multiple shelves, however this type of equipment is not suitable for housing bioreactors.

What is needed is the ability to stack multiple bioreactors one on top of another, closely spaced side by side, in a system that is simple to load, operate and maintain. Ideally such bioreactors should be capable of tradition fed batch manufacturing where cells are cultured typically over 7 to 21 days, as well as perfusion type manufacturing where cells can be cultured for longer periods, but waste products are continually or regularly removed, and biomolecules may be harvested.

A solution to the above mentioned needs has been proposed in unpublished and co-pending patent application GB1518426.0, the contents of which are incorporated herein by reference. Therein, a stackable bioreactor was proposed, which saved on floor space, was capable of providing small batch sizes used in autologous therapies, and did not require clean room conditions. One important aspect of that prior design was a removable rocking platform on which a cell culture bag could be supported during culturing. However, the inventors of the present invention realised that in stacking bioreactors, that platform requires careful design to make it easier to use (removing and loading whilst supporting a bag containing, essentially, liquids in a confined area) and easier to dismantle for cleaning.

SUMMARY OF THE INVENTION

The invention provides an arrangement according to claim 1 having preferred features defined by claims dependent on claim 1.

The invention extends to any combination of features disclosed herein, whether or not such a combination is mentioned explicitly herein. Further, where two or more features are mentioned in combination, it is intended that such features may be claimed separately without extending the scope of the invention.

BRIEF DESCRIPTION OF THE DRAWINGS

The invention can be put into effect in numerous ways, illustrative embodiments of which are described below with reference to the drawings, wherein:

FIGS. 8 to 14 shows detailed views of a modified tray and tray support.

The invention, together with its objects and the advantages thereof, may be understood better by reference to the following description taken in conjunction with the accompanying drawings, in which like reference numerals identify like elements in the Figures.

Referring to FIG. 1a there is shown biomanufacturing apparatus 1 including a generally self-contained instrument 10 which includes a generally cuboid or box-shaped housing 20 having generally flat upper and bottom sides 22 and 24. The bottom side includes four adjustable height feet 26, only two of which are visible in FIG. 1a. The box shaped housing allows stacking of plural instruments to form a biomanufacturing system. In practice, for convenience, the stack will be two or three high on a benchtop 5, as schematically illustrated in FIG. 1b, although there is no reason why the stack could not be higher. The instrument also includes a door 25, shown open and cut away for in order to shown the remaining parts of the instrument more clearly. The door is hinged at hinges 28 to the front vertical edge of the housing, so that it opens about a vertical hinge axis to expose or enclose an insulated chamber 30 inside the housing 20. The chamber 30 is sealed when the door is closed by an elastomeric seal 32 extending around the whole periphery of the inner face of the door and cooperating with a seal face 31 extending in a complementary manner around the front edges of the housing 20. No light enters the chamber 30 when the door 25 is closed. This negates light effects on the cell culture.

Figures 1A, 1B:
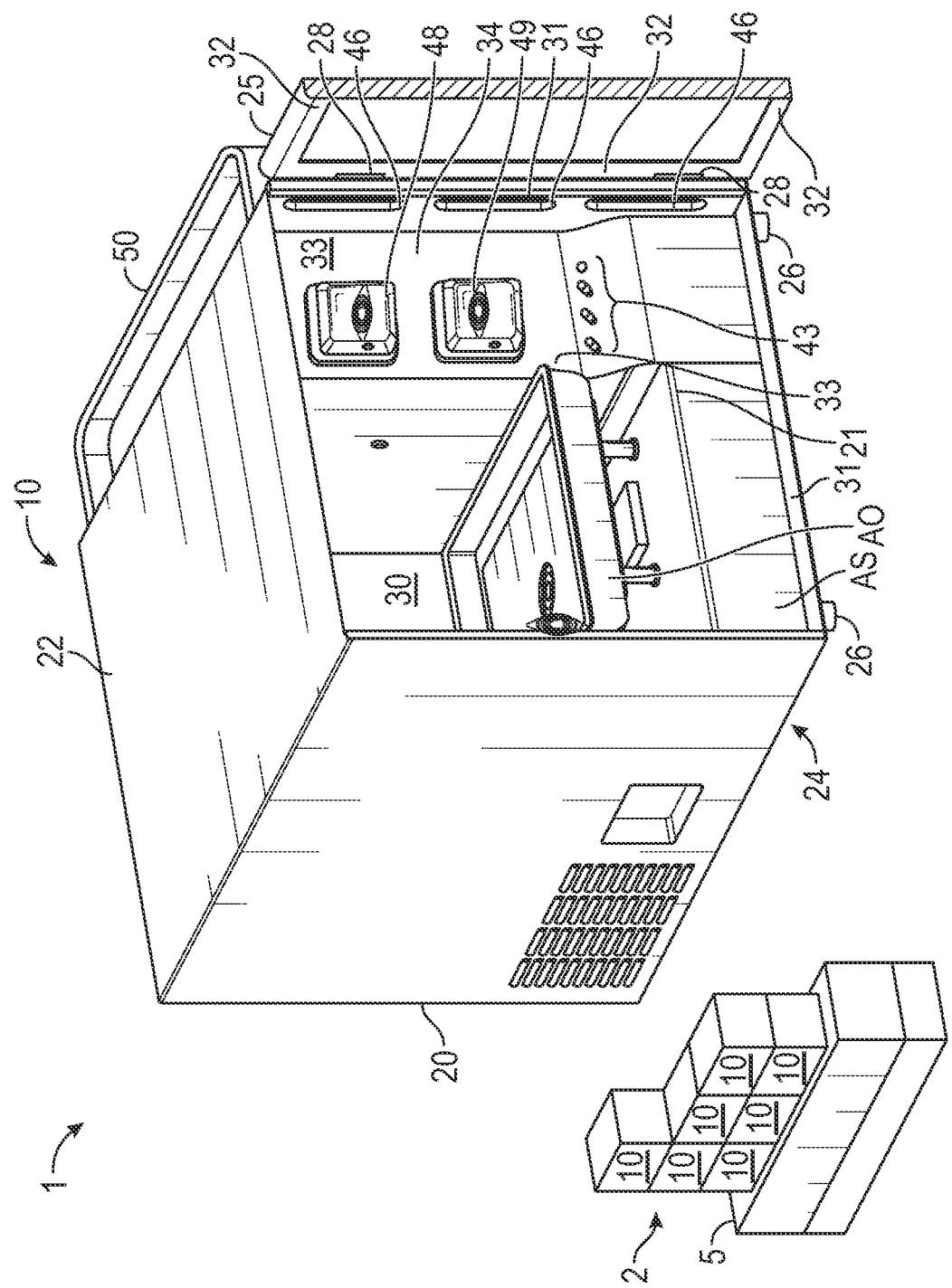
FIG. 1a shows a pictorial view of an embodiment of biomanufacturing apparatus.
FIG. 1b shows the apparatus of FIG. 1a stacked to form a biomanufacturing system 2.

The chamber 30 has a main chamber 35 and an antechamber 33 leading to the main chamber 35. The main chamber includes a bioreactor tray 40 for example for supporting a cell culture bag—a cell bag herein, supported by a rocking tray support 45 described in more detail below. The rocking mechanism is protected by a cover plate 21. The antechamber 33 includes a panel 34 supporting two peristaltic pumps only the fluid handling heads 48 and 49 of which extend into the antechamber 33, the electrical parts of which are behind the panel 34. The panel also includes connections 43 described in more detail below. The antechamber 33 includes openings 46 defining a route for conduits extending to an external storage area which includes a bag hanging rack 50.

Figure 2:
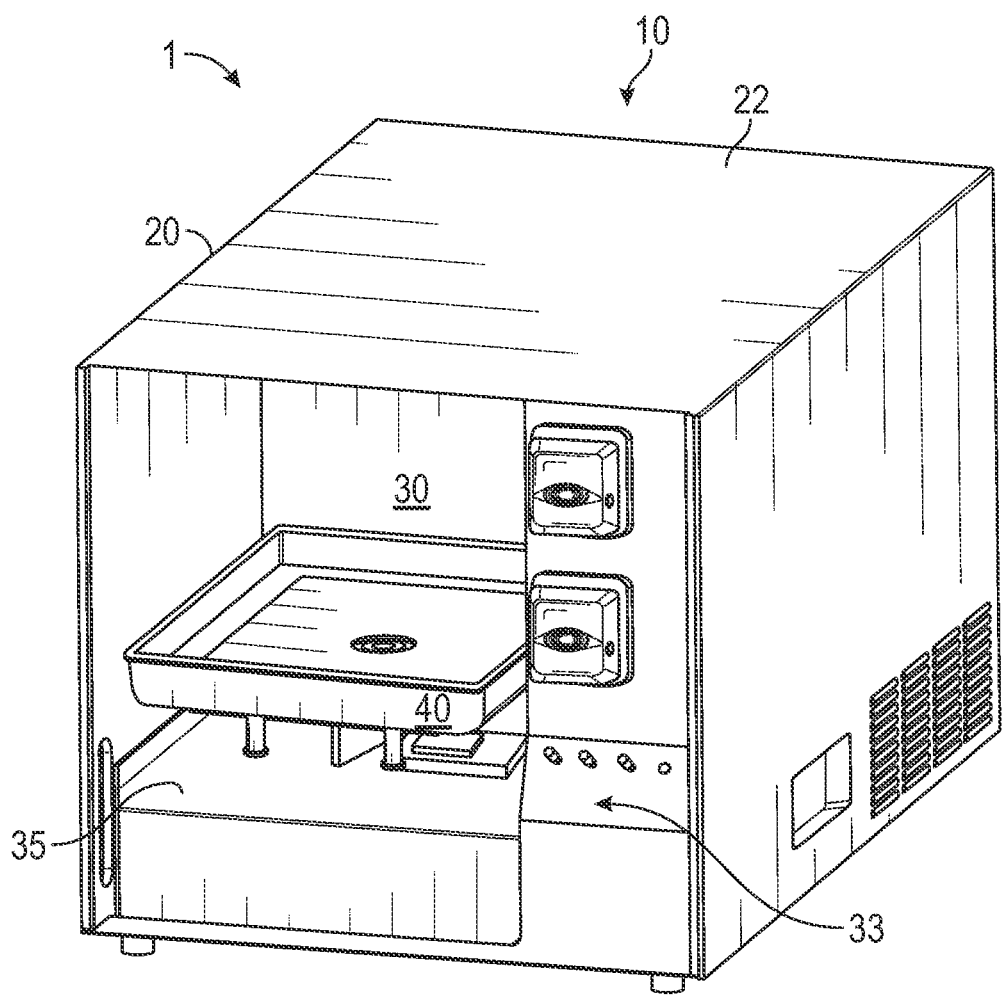
FIG. 2 shows a different pictorial view of the apparatus shown in FIG. 1.

FIG. 2 is a different view of the instrument 10 shown in FIG. 1, with the door 25 and bag rack removed 50, in order to show the remaining parts of the instrument more clearly.

Figure 3:
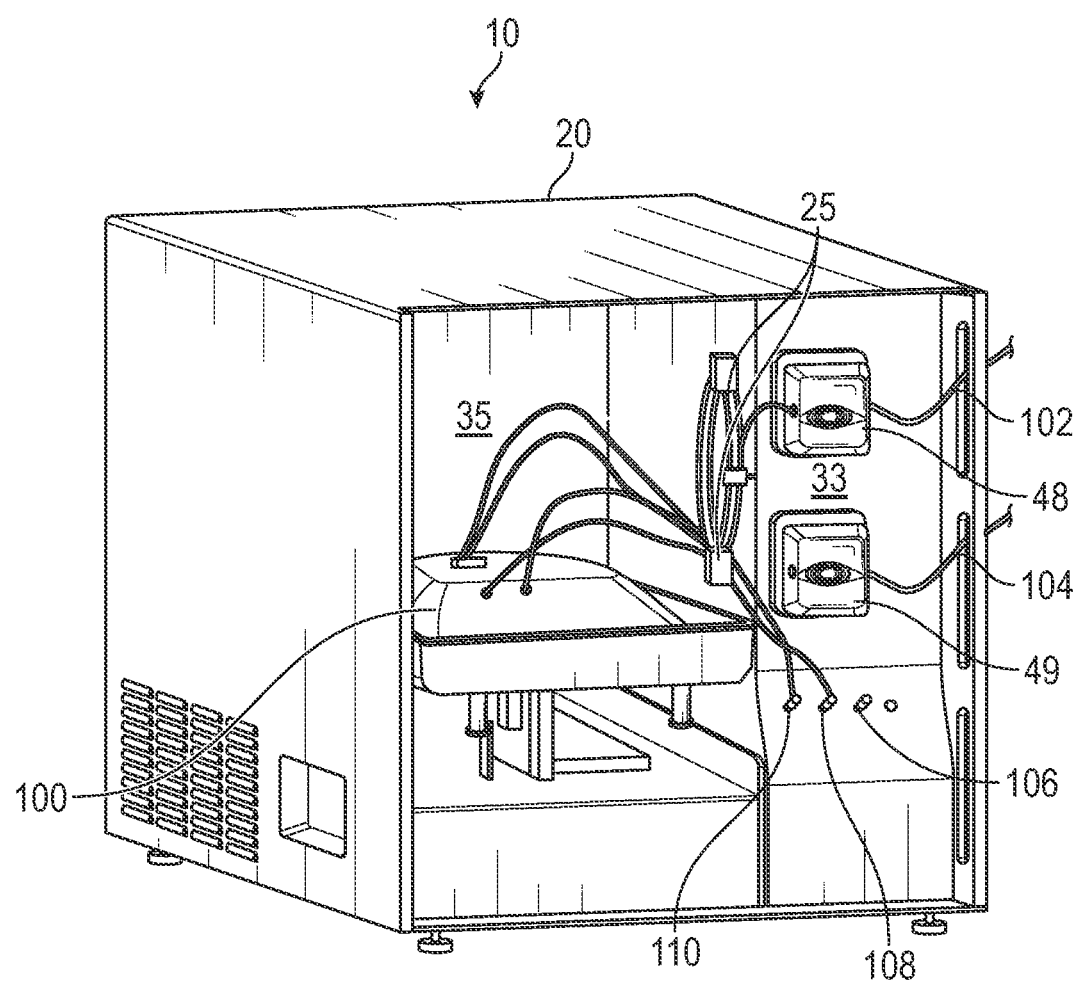
FIG. 3 shows another pictorial view of the apparatus shown in FIG. 1, including a bioreactor loaded inside the apparatus.

FIG. 3 shows the instrument 10 of FIGS. 1 and 2, but loaded with a bioreactor 100, in this instance, in the form of a flexible bag 100, as well as various paths linking the bioreactor to the instrument, including: a fluid supply conduit 102 feeding the bioreactor with a known mixture of fluids to promote cell growth via the peristaltic pump head 48, a fluid removal conduit 104 for drawing off fluids from the reactor for the purpose of removing waste components expressed by cells in the bioreactor via a filter incorporated in the bag 100 and via the peristaltic pump head 49; a gas feed conduit 106; and paths, for example electrically conductive paths 106, 108 and 110 for example electrical wires, for various sensors within or adjacent the bioreactor, for example a pH sensor, and a dissolved oxygen (DO) sensor. The conduits and paths can be kept in place by one or more hangers 23.

Figure 4:
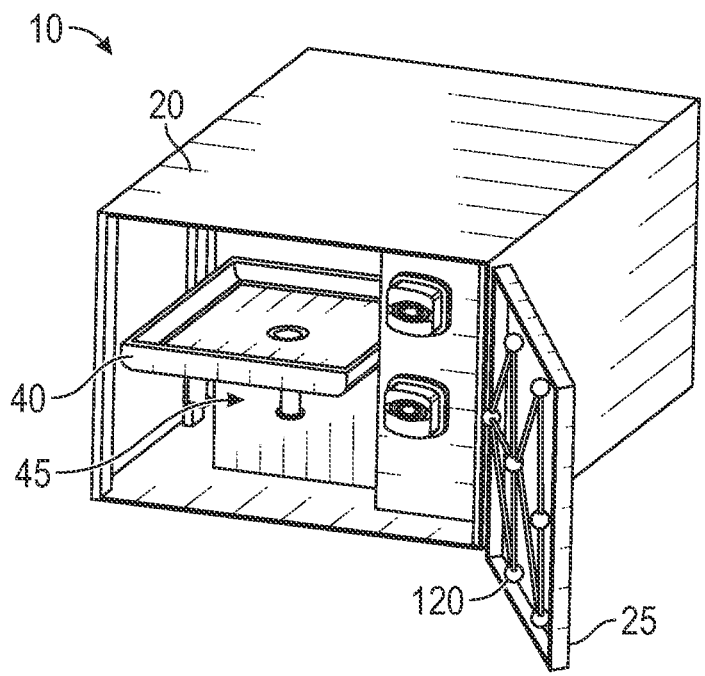
FIGS. 4 and 5 show two pictorial views of a further embodiment of biomanufacturing apparatus, in different configurations.
Figure 5:
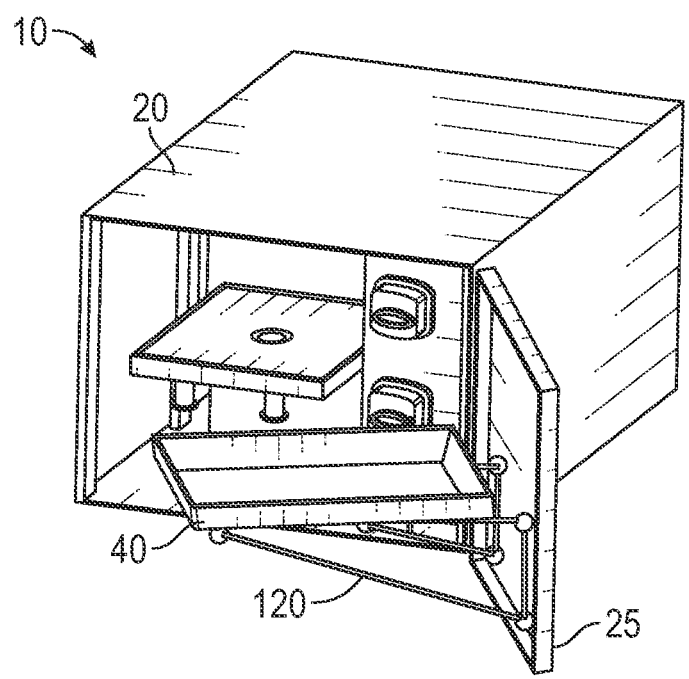

FIGS. 4 and 5 show an embodiment of the instrument 10 including the door 25. The tray 40 in this embodiment is removable from the tray support 45 by sliding motion and can rested on a collapsible stand 120, in turn hung on the hinged door 25. In use, the door 25 can be opened, the stand 120 can be dropped down, and the tray 40 (without or without a bioreactor in place) can be slid away from the support 45 and manually moved onto the stand. It will be noted that the tray 40 has an open mid-section. This open section accommodates a bioreactor, which has clips that clip onto the tray 40 sides so that the bioreactor does not fall through the middle of the tray. Returning the tray full or empty back into the chamber 30, allows the frame 120 to be folded away and the door 25 to be closed shut.

Figure 6A:
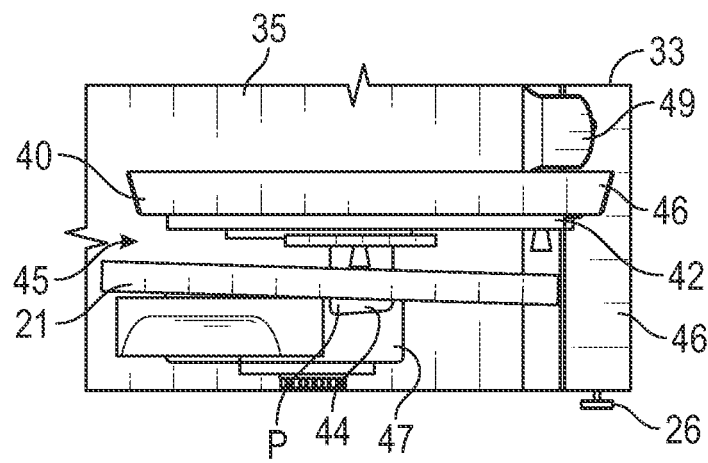
FIGS. 6a, 6b, 6c and 6d show a partial sectional view of the apparatus shown in FIGS. 1 and 2.
Figure 6B:
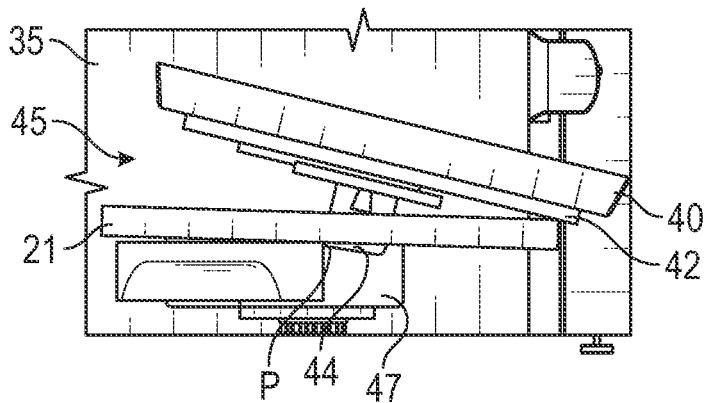
Figure 6C:
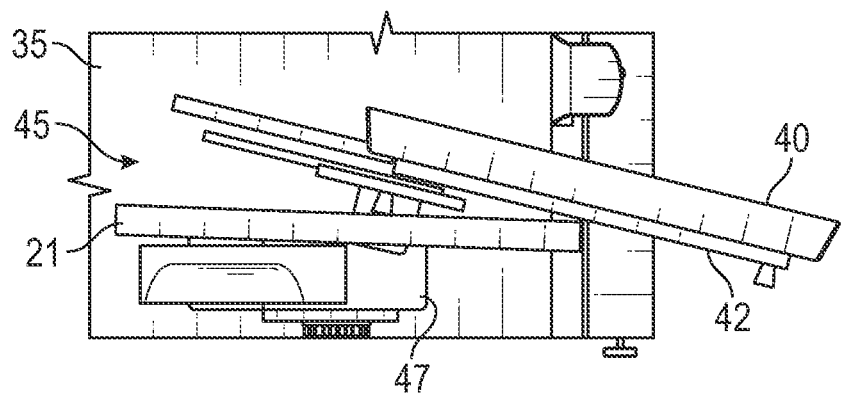
Figure 6D:
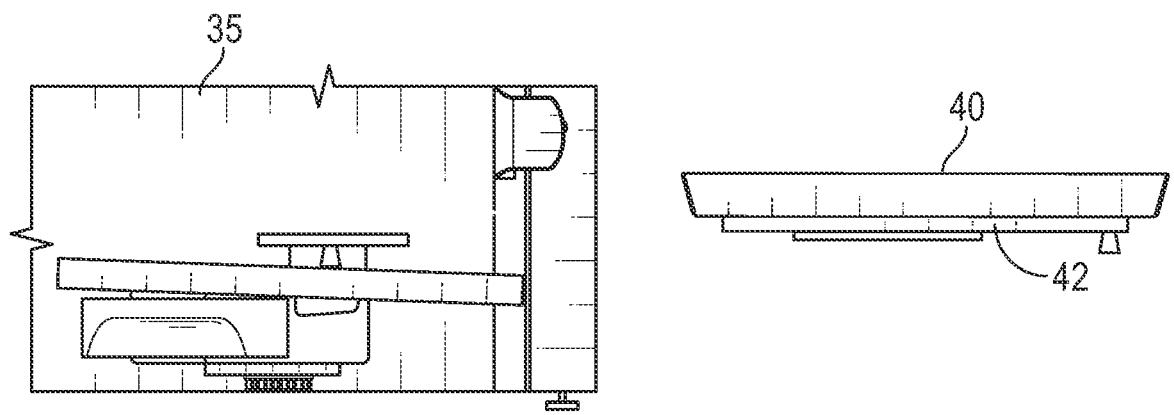

FIGS. 6a, 6b, 6c and 6d each show a sectional view of the main chamber 35 illustrated in FIGS. 1 to 3, and the components housed therein. Those components include the removable tray 40 and the rocking tray support 45. The tray support 45 is formed from an electrically heated plate 42 which is in direct contact with the bottom of a bioreactor in use, a pivotable plate holder 44 which releasably holds the heated plate and an electrical stepper motor driving rocking mechanism 47 which moves the plate holder 44 back and forth about a pivot axis P below the tray 40 through a predefined angle of about 25-35 degrees. The support 45 is controllable in use so that it stops in any position, but in particular in the forward slopping position shown in FIG. 6b, which enables the tray 40 and plate 42 to be slid forward together whilst the plate holder 44 stays in position, to a new position as illustrated in FIG. 6c, where the tray is more readily accessible for loading or unloading rather than having to remove it as shown in the embodiment of FIGS. 4 and 5. In the position shown in FIG. 6c the conduits and paths between the bioreactor and the instrument, as mentioned above, can be connected or disconnected more easily. The tray 40 and plate 42 can be removed completely as shown in FIG. 6d, for example, for cleaning purposes. A cover plate 21 protects the motor and other electrical parts.

Figure 7:
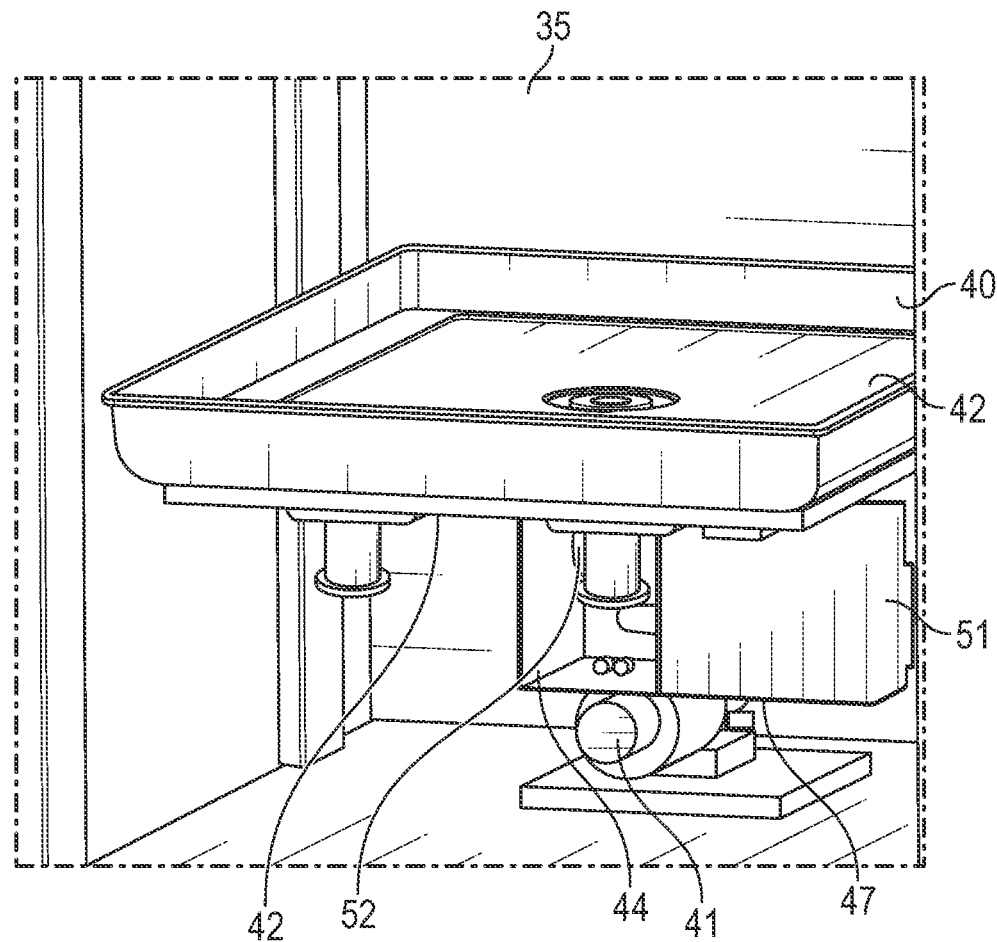
FIG. 7 to shows an enlarged partial view of the apparatus shown in FIGS. 1 and 2.

FIG. 7 shows the rocking mechanism in more detail view from the front, door, side of the instrument looking into the main chamber 35 with the cover plate 21 removed. A stepper motor 51 of the rocking mechanism 47 is shown as well as a reduction pinion gear pair 52 driven by the stepper motor and driving the plate support 44 to rotate back and forth. In this view a load sensor, in the form of a load cell 41 is visible which in use is used to measure the quantity of fluid added or removed from the bioreactor, and cell culture control.

FIGS. 8 to 14 show details of a modified cell bag bioreactor tray 240 and its support 245 which have similar functionality to the tray and support 40/45 described above and where like parts have like reference numerals but in the latter embodiment the reference numerals are additionally preceded by the number 2.

In the embodiment, shown in FIG. 8, there are three main parts: the tray frame 240 which holds a cell bag; a tray heating plate 242, which is in direct contact with a cell bag resting in the tray frame; and the support 245 in turn rigidly connected to a rocking and drive system 247 & 244, the support 245 including electrical connections to power the heating plate 242. The support 245 has a female vee slot 250 which cooperates with a complementary male vee slot 252 on the heating plate 242 to hold the two components 242 and 245 in removable sliding engagement, together providing complementary formations which allow easier access to a cell bag mounted on the tray 245. A spring biased pin 254 extends through both components and, together with the complementary vee slots, holds these two components together. The pin 254 can be manually urged out of engagement of with the heater plate 242 in the direction of arrow A to allow the heater plate to slide relative the support 245 in the vee slot 250. In an alternative embodiment the pin 254 can be electromechanically operable.

FIG. 9 shows more details of the tray 240, and the heater plate 242, and more clearly shows two additional sprung pins 264. Additionally, tray 240 includes at opposed ends cell bag securing cleats 268 which hold the crimped ends of a cell bag in place to stop it falling through the open bottomed tray 240 when the tray 240 is removed from the heater plate 242 in use.

FIG. 10 shows an end view of the parts shown in of FIG. 9, and FIG. 11 shows the parts in FIG. 9 but in a partially dismantled condition. Tray 240 can be slid in the direction of arrow B by manually pulling the pins 264 downwardly in the direction of arrows A. Where an automatic configuration is envisaged the pins 264 may be electromechanically actuated. In this embodiment, the tray 240 includes two separable parts: an upper frame 271 and a lower frame 270—on which are supported the pins 264. The lower frame supports the upper frame during disassembly and reassembly.

Siding of the tray 240 (including the upper and lower frames 270/271) on the heater plate 242 is permitted by means of a tee formation 280 and a complementary tee slot 281, one mounted to the heater plate 242 and one mounted to the lower frame 270, which together allow sliding in the direction of arrow B and the opposing direction. Stops associated with the tee slots prevent complete removal of the lower frame 270 from the heater plate 242, in use.

FIGS. 12 and 13a/b show further details of tray features. In FIG. 12, the upper frame 271 is shown removed completely from the lower frame 270. In FIGS. 13a and 13b a sectional view is shown which illustrates the features which enable that complete removal. In particular, the upper frame 271 has opposed partial grooves 283 which cooperate with opposed partial tongues 284 formed in the heater plate. Once the tray upper frame 240 has reached substantially its complete sliding extremity, these tongues and grooves no longer cooperate, and allow the upper frame 271 to be lifted away from its supporting lower frame 270. The position of the grooves 283 and tongues may be reversed 284.

FIG. 14 is a sectional view showing the various parts discussed above in more detail.

Reassembly of the upper frame to the lower frame, and the sliding of the resulting tray assembly, is brought about by reversing the motions described above.

In this way a rocking cell bag support is conceived which is easy to use, allowing convenient insertion and removal of a cell bag, as well as being readily dismantleable for cleaning. For more convenient use a frame position sensor is employed to check alignment of the upper frame 271 with the heater plate 242 in use.

Although embodiments have been described and illustrated, it will be apparent to the skilled addressee that additions, omissions and modifications are possible to those embodiments without departing from the scope of the invention claimed.

The invention claimed is:

1. A biomanufacturing apparatus, comprising: a housing including top and bottom faces, which allow stacking of plural housings;
   an access door at a front side of the housing;
   a substantially enclosed bioreactor chamber inside the housing accessible via the door; and
   a further substantially enclosed region inside the housing containing at least one of electrical parts and electronic control components,
   wherein the chamber comprises:
       a tray for supporting a bioreactor, and
       a tray support including a mechanism for rocking the tray in use,
       the tray having complementary formations allowing a secured sliding movement of the tray relative to the tray support, relative to the mechanism for rocking, and relative to the at least one of electrical parts and electronic control components toward the front side and at least partly out of the chamber to allow more convenient access to the bioreactor;
   and wherein the tray support includes a heater plate mounted to the mechanism for rocking, by means of complementary demountable formations.

2. The apparatus of claim 1, wherein the complementary formations include a tee slot and a tee formation.

3. The apparatus of claim 1, wherein the tray is separable from the tray support once the tray support has been moved toward the front side.

4. The apparatus of claim 1, wherein the heater plate forms the underside of the tray such that a bioreactor is supported directly on its underside by the heater plate in use.

5. The apparatus of claim 1, wherein the relative movement of said complementary formations is inhibited by at least one sprung locking pin.

6. The apparatus of claim 1, wherein the complementary demountable formations comprise a dovetail and dovetail slot.

7. The apparatus of claim 1, wherein the complementary demountable formations are inhibited by at least one sprung locking pin.

8. The apparatus of claim 1, wherein the complementary formations constrain the tray to remain slidably secured to the tray support during the secured sliding movement.

9. A biomanufacturing apparatus, comprising:
   a housing including top and bottom faces, which allow stacking of plural housings;
   an access door at a front side of the housing;
   a substantially enclosed bioreactor chamber inside the housing accessible via the door; and
   a further substantially enclosed region inside the housing containing at least one of electrical parts and electronic control components,
   wherein the chamber comprises:
       a tray for supporting a bioreactor, and
       a tray support including a mechanism for rocking the tray in use, the tray having complementary formations allowing a secured sliding movement of the tray relative to the tray support, relative to the mechanism for rocking, and relative to the at least one of electrical parts and electronic control components toward the front side and at least partly out from the chamber to allow more convenient access to the bioreactor,
   wherein the tray support includes a heater plate mounted to the mechanism for rocking, by means of complementary demountable formations,
   wherein the heater plate forms the underside of the tray such that a bioreactor is supported directly on its underside by the heater plate in use, and
   wherein the relative movement of at least one of said complementary formations and complementary demountable formations is inhibited by at least one sprung locking pin.

10. The apparatus of claim 9, wherein the complementary demountable formations comprise a dovetail and dovetail slot.

11. The apparatus of claim 9, wherein the complementary demountable formations are inhibited by at least one sprung locking pin.

12. The apparatus of claim 9, wherein the complementary formations are inhibited by at least one sprung locking pin.

13. The apparatus of claim 9, wherein the complementary formations include a tee slot and a tee formation.

14. The apparatus of claim 9, wherein the tray is separable from the tray support once the tray support has been moved toward the front side.

15. The apparatus of claim 9, wherein the complementary formations constrain the tray to remain slidably secured to the tray support during the secured sliding movement.

* * * * *